United States Patent
Veverka et al.

(10) Patent No.: US 11,344,485 B2
(45) Date of Patent: May 31, 2022

(54) HAIR COLOURING OR BLEACHING PRODUCTS, AND COMPOSITIONS THEREOF, WITH ALKALI CANCELING EFFECT

(71) Applicant: HFC Prestige International Holdings Switzerland S.A.R.L., Petit-Lancy (CH)

(72) Inventors: Frank Veverka, Zwingenberg (DE); Manfred Guenther Schmitt, Bensheim (DE); Rebecca Knobloch, Darmstadt (DE)

(73) Assignee: Wella International Operations Switzerland Sàrl, Petit-Lancy (CH)

( * ) Notice: Subject to any disclaimer, the term of this patent is extended or adjusted under 35 U.S.C. 154(b) by 0 days.

(21) Appl. No.: 17/261,797

(22) PCT Filed: Jul. 19, 2019

(86) PCT No.: PCT/EP2019/069481
§ 371 (c)(1),
(2) Date: Jan. 20, 2021

(87) PCT Pub. No.: WO2020/016404
PCT Pub. Date: Jan. 23, 2020

(65) Prior Publication Data
US 2021/0259935 A1    Aug. 26, 2021

(30) Foreign Application Priority Data

Jul. 20, 2018 (EP) ..................... 18184835

(51) Int. Cl.
| A61Q 5/10 | (2006.01) |
| A61K 8/24 | (2006.01) |
| A61K 8/22 | (2006.01) |
| A61K 8/23 | (2006.01) |
| A61K 8/362 | (2006.01) |
| A61Q 5/06 | (2006.01) |
| A61Q 5/08 | (2006.01) |

(52) U.S. Cl.
CPC .................. *A61K 8/24* (2013.01); *A61K 8/22* (2013.01); *A61K 8/23* (2013.01); *A61K 8/362* (2013.01); *A61Q 5/065* (2013.01); *A61Q 5/08* (2013.01); *A61Q 5/10* (2013.01); *A61K 2800/4322* (2013.01); *A61K 2800/4324* (2013.01); *A61K 2800/88* (2013.01)

(58) Field of Classification Search
CPC ... A61Q 5/10; A61Q 5/08; A61K 8/22; A61K 2800/4324; A61K 2800/88; A61K 2800/4322; A61K 8/55; A61K 8/24; A61K 8/362
USPC ............................................................ 8/405
See application file for complete search history.

(56) References Cited

U.S. PATENT DOCUMENTS

| 8,460,397 B2 * | 6/2013 | Lim ...................... A61K 8/4926 |
| | | 8/405 |
| 2005/0000035 A1 | 1/2005 | Chan et al. |
| 2007/0067925 A1 * | 3/2007 | Javet ...................... A61Q 5/065 |
| | | 8/405 |
| 2007/0220684 A1 * | 9/2007 | Narasimhan ............. A61K 8/22 |
| | | 8/405 |
| 2011/0067723 A1 * | 3/2011 | Bureiko ................... A61K 8/29 |
| | | 132/208 |
| 2011/0168201 A1 * | 7/2011 | Bureiko ................. A61K 8/604 |
| | | 132/208 |
| 2015/0328100 A1 * | 11/2015 | Mohring .................. A61K 8/23 |
| | | 8/431 |
| 2016/0199291 A1 * | 7/2016 | Grit .......................... A61K 8/31 |
| | | 8/409 |
| 2017/0360662 A1 * | 12/2017 | Azizova ................... A61Q 5/10 |

FOREIGN PATENT DOCUMENTS

| EP | 0435012 | * | 7/1991 | ............... A61Q 5/10 |
| EP | 0435012 A1 | | 7/1991 | |
| JP | 2006182685 A | | 7/2006 | |
| JP | 2007262001 A | | 10/2007 | |
| JP | 2008189584 A | | 8/2008 | |

OTHER PUBLICATIONS

International Search Report issued in connection with PCT Application PCT/EP2019/069481 dated Sep. 30, 2019.

* cited by examiner

*Primary Examiner* — Eisa B Elhilo
(74) *Attorney, Agent, or Firm* — Victoria Friedman; Dennemeyer & Associates LLC

(57) ABSTRACT

It is provided herewith a hair treating product comprising an oxidizing component and a tint component; a hair treating composition obtained upon mixing of the oxidizing component and the tint component; the use of the oxidizing component in a hair treating product, for cancelling the alkalinity of a tint component; and an oxidizing component comprising a buffer system. The hair treating product, and the corresponding hair treating composition, is particularly useful for colouring or bleaching hair. It is useful for providing permanent or demi-permanent coloration or bleaching to keratin fibers.

11 Claims, No Drawings

HAIR COLOURING OR BLEACHING PRODUCTS, AND COMPOSITIONS THEREOF, WITH ALKALI CANCELING EFFECT

CROSS-REFERENCE TO RELATED APPLICATIONS

This is a 35 U.S.C. 371 National Stage Patent Application of International Application No. PCT/EP2019/069481, filed Jul. 19, 2019, which claims priority to European application 18184836.9, filed Jul. 20, 2018, each of which is hereby incorporated by reference in its entirety.

FIELD OF THE INVENTION

It is provided herewith a hair treating product comprising an oxidizing component and a tint component; a hair treating composition obtained upon mixing of the oxidizing component and the tint component; the use of the oxidizing component in a hair treating product, for cancelling the alkalinity of a tint component; and an oxidizing component comprising a buffer system. The hair treating product and the corresponding hair treating composition are particularly useful for colouring or bleaching hair. They are useful for providing permanent or demi-permanent coloration or bleaching to keratin fibers.

BACKGROUND OF THE INVENTION

The permanent alteration of the hair color by the application of hair dyes is well known. In order to provide the consumer with the shade and the intensity of color desired, a complex chemical process is utilized. Permanent hair dyeing formulations typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of color. This reaction typically takes place in an aggressive environment up to a pH of 11 in the presence of an alkalizing agent and an oxidizing agent. Direct dyes can also be used depending on the desired hair color. Typically, an oxidizing composition (oxidizing component) comprising the oxidizing agent and a dye composition (also called tint or dye component) comprising the alkalizing agent and if present the precursors dye molecules are mixed shortly before use. The consumer repeats this process regularly in order to maintain the desired hair color and shade and the intensity of color and to ensure continual, even coverage of the hair including coverage of new hair growth. A wide variety of developers and couplers have been employed in oxidative products, systems and compositions. Different treatments can be carried out, including permanent and demi permanent oxidative colouring treatments. Permanent and demi permanent oxidative colouring techniques are respectively referred as Level 3 and Level 2. Level 2 colouring techniques usually differ from Level 3 in that the tint component has a lower alkaline concentration, and a lower concentration of dyes, while the oxidizing component has a lower peroxide strength. Level 2 techniques allow obtaining coloured hair, however with less lift and less grey coverage than Level 3 techniques.

While hair colouring or bleaching techniques have been improving over time, conventional techniques do not necessarily prevent the damages to the treated hair. In addition, current techniques Level 2 and Level 3 usually require relying upon different oxidizing components and different line-ups of many different tint components (different shades and tones). In salons, where hairdressers shall offer services for colouration or bleaching over a large spectrum, it means that they should have different, specific oxidizing components for certain colouring or bleaching line-ups, with usually different line-ups of tint components for Level 2 techniques and Level 3 techniques.

One need that still remains is to provide hair colouring or bleaching product, and the corresponding hair colouring or bleaching composition, reducing, or even preventing the damages of hair. There is also the need for providing simplified line-up of hair colouring or bleaching product, and the corresponding hair colouring or bleaching composition. Particularly, there is the need for providing a universal line-up of tint components, for use both for Level 2 and Level 3 colouration. In addition, there is always the need for providing components and compositions being safe for use, both for the unskilled customer and the hairdresser manipulating such products very frequently. To this extent, there is the need for providing components and compositions having pH ranges within safe boundaries, i.e. not having extreme acidic or alkaline pH.

SUMMARY OF THE INVENTION

The present invention relates to hair treating product, said product comprising: (1) an oxidizing component having an acidic pH above 1.5 and comprising: from 1% to 16% of at least one source of oxidizing agent by total weight of the oxidizing component;
 a buffer system; said buffer system comprising:
 a buffering acidic compound;
 a buffering alkali compound;
 wherein the buffering acidic compound is selected from the group consisting of organic and inorganic acids, and the corresponding buffering alkali compound is selected from the group consisting of alkali metal salts, amino acids, and salts thereof;
 wherein the buffering acidic compound and the buffering alkali compound are present in amounts sufficient for providing a buffering effect equivalent to a buffer system comprising from 0.5% to 4% phosphoric acid and from 0.4 to 3.5% disodium phosphate by total weight of the oxidizing component, and with a weight ratio of phosphoric acid to disodium phosphate comprised from 1:1 to 10:1; and preferable from 1:1 to 5:1.
 wherein the buffering capacity of the buffer system is superior by a factor from 5 to 40 times than the buffer system of a conventional oxidizing component comprising about 0.1% of a buffering acidic compound being phosphoric acid and about 0.1% of a buffering alkali compound being disodium phosphate by total weight of the oxidizing component;
 (2) a tint component having an alkali pH from 7.5 to 11.5 and comprising;
 from 0.5% to 12% of at least one source of alkalizing agent by total weight of the tint component.

The present invention also relates to a ready-to-use hair treating composition, said composition having a pH from 6.0 to 10.5 and comprising:
 from 0.5% to 8% an oxidizing agent;
 from 0.25% to 6% of an alkalizing agent;
 wherein said composition is obtained from the mixing of an oxidizing component having an acidic pH above 1.5 and a tint component having a alkali pH from 7.5 to 11.5, said oxidizing component comprising a buffer system according to the hair treating product as defined hereinbefore;

wherein the composition has a reduction of pH from 0.5 units, preferably from 0.5 to 6 units, more preferable from 0.5 to 4 units, versus a hair treating composition obtained from a conventional oxidizing component as defined hereinbefore.

The present invention also relates to the use of an oxidizing component as well as an alkali cancelling oxidizing component.

The inventors have demonstrated that the above needs may be met with the provision of a hair treating (colouring or bleaching) product, and the corresponding hair treating (colouring or bleaching) composition, exhibiting an alkali cancelling effect. Such effect could be attained by designing a specific buffer system, present in the oxidizing component, allowing lowering down the pH of the hair treatment composition (obtained upon mixing the tint and the oxidizing components), without formulating an oxidizing component with a too low pH, which could be otherwise potentially harmful to the customer and/or the hairdresser.

DETAILED DESCRIPTION OF THE INVENTION

Definitions

While the specification concludes with claims which particularly point out and distinctly claim the invention, it is believed the present invention will be better understood from the following description.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. When more than one composition is used during a treatment, as in mixing of the components of a typical oxidative dye product, the total weight to be considered is the total weight of all the compositions applied on the hair simultaneously (i.e. the weight found "on head") unless otherwise specified. The term "weight percent" may be denoted as "wt. %" herein.

As used herein the term "hair" to be treated may be "living" i.e. on a living body or may be "non-living" i.e. in a wig, hairpiece or other aggregation of non-living keratinous fibers.

Mammalian, preferably human hair is preferred. However wool, fur and other keratin containing fibers are suitable substrates for the compositions according to the present invention.

By "hair coloring" composition it is meant a composition suitable for changing the color of hair. The hair coloring composition is referred hereinafter as "the composition", unless otherwise specified. The hair coloring composition can comprise oxidative dye precursors, direct dyes or even no, or substantially no, dyes in case of bleaching only compositions where the change of color is mainly caused by the degradation of the natural melanin contained in the hair shaft by the oxidizing agent. The term "hair coloring" composition as used herein covers hair bleaching and hair oxidative dyeing products.

As used herein, the term "chromophore" means the part of the dye compound responsible for its color.

As used herein, the term "physiologically compatible salts" means salts that are suitable to be used with humans and have limited to no irritancy to humans.

As used herein, the term "substantially free" means that the hair dyeing compositions comprises less than 1%, preferably less than 0.1%, more preferably less than 0.01%, still more preferably is free of, a compound.

As used herein, the terms "developer" and "primary intermediary" are interchangeable. As used herein, the term "compound" encompasses any tautomeric compound, if applicable, and except if stated otherwise. Hence, it is to be understood that when it is referred to a particular structure, all of the reasonable additional tautomeric structures are included. In the art, tautomeric structures are frequently represented by one single structure and the method described herein follows this general practice. For example, 2-mercaptopyridine (I) may exist under known conditions in the pyridine-2-thione tautomer form (II).

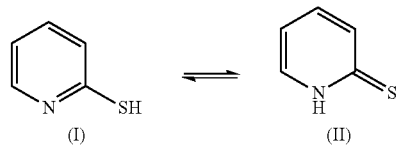

As used herein, the term "compound" encompasses any isomeric compound, if applicable, and except if stated otherwise. Hence, it is also understood that E, Z isomers may be involved, and that all of the reasonable additional E, Z isomers are included. For example, (E)-diphenyldiazene (III) converts under known conditions to (Z)-diphenyldiazene (IV), which is also reversible.

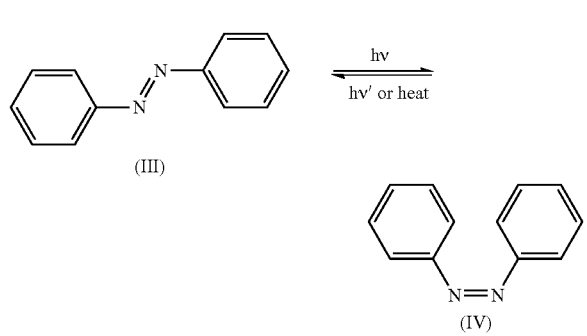

As used herein, the term "corresponding buffering alkali compound" particularly means the alkali compound (or salt) of the organic or inorganic acid present. For example, corresponding buffering alkali compounds of phosphoric acid—or phosphate salts—are alkali metal of phosphoric acid, such as disodium phosphate.

In a first aspect, the present invention relates to hair treating product, said product comprising: (1) an oxidizing component having an acidic pH above 1.5 and comprising:

from 1% to 16% of at least one source of oxidizing agent by total weight of the oxidizing component;
a buffer system; said buffer system comprising:
a buffering acidic compound;
a buffering alkali compound;
wherein the buffering acidic compound is selected from the group consisting of organic and inorganic acids, and the corresponding buffering alkali compound is selected from the group consisting of alkali metal salts, amino acids, and salts thereof;

wherein the buffering acidic compound and the buffering alkali compound are present in amounts sufficient for providing a buffering effect equivalent to a buffer system comprising from 0.5% to 4% phosphoric acid and from 0.4 to 3.5% disodium phosphate by total weight of the oxidizing component; and with a weight ratio of phosphoric acid to disodium phosphate comprised from 1:1 to 10:1, preferably from 1:1 to 5:1;

wherein the buffering capacity of the buffer system is superior by a factor from 5 to 40 times than the buffer system of a conventional oxidizing component comprising about 0.1% of a buffering acidic compound being phosphoric acid and about 0.1% of a buffering alkali compound being disodium phosphate by total weight of the oxidizing component;

(2) a tint component having an alkali pH from 7.5 to 11.5, and comprising;

from 0.5% to 12% of at least one source of alkalizing agent by total weight of the tint component.

It may be provided particularly a hair treating product:

wherein the oxidizing component comprises from 1% to 6% of at least one source of oxidizing agent;

wherein the buffering acidic compound and the buffering alkali compound are present in amounts sufficient for providing a buffering effect equivalent to a buffer system comprising from 0.5% to 3% phosphoric acid and from 0.4% to 2% disodium phosphate by total weight of the oxidizing component; and, wherein the tint component comprises from 0.5% to 1.5%, alternatively from 0.5% to 0.75%, of one source of alkalizing agent by total weight of the tint component.

It may also be provided particularly a hair treating product: wherein the oxidizing component comprises from 1.5% to 9.0% of at least one source of oxidizing agent;

wherein the buffering acidic compound and the buffering alkali compound are present in amounts sufficient for providing a buffering effect equivalent to a buffer system comprising from 1.0% to 3.5% phosphoric acid and from 1% to 2.5% disodium phosphate by total weight of the oxidizing component; and, wherein the tint component comprises from 0.75% to 6.0%, alternatively from 0.75% to 3.0%, of one source of alkalizing agent by total weight of the tint component.

It may also be provided a hair treating product:

wherein the oxidizing component comprises from 2.0% to 16.0% of at least one source of oxidizing agent;

wherein the buffering acidic compound and the buffering alkali compound are present in amounts sufficient for providing a buffering effect equivalent to a buffer system comprising from 1.5% to 4.0% phosphoric acid and from 1% to 3.5% disodium phosphate by total weight of the oxidizing component; and, wherein the tint component comprises from 3.0% to 12.0%, alternatively from 3.0% to 6.0%, of one source of alkalizing agent by total weight of the tint component.

In an alternative first aspect, the present invention relates to hair treating product, said product comprising:

(1) an oxidizing component having an acidic pH above 1.5 and comprising from 1% to 16% of at least one source of oxidizing agent by total weight of the oxidizing component;

(2) a tint component having an alkali pH from 7.5 to 11.5, and comprising from 0.5% to 12%, alternatively from 0.5% to 6% of at least one source of alkalizing agent by total weight of the tint component;

(3) a third component comprising a buffer system; said buffer system comprising:

a buffering acidic compound;
a buffering alkali compound;

wherein the buffering acidic compound is selected from the group consisting of organic and inorganic acids, and the corresponding buffering alkali compound is selected from the group consisting of alkali metal salts, amino acids, and salts thereof;

wherein the buffering acidic compound and the buffering alkali compound are present in amounts sufficient for providing a buffering effect equivalent to a buffer system comprising from 0.5% to 4% phosphoric acid and from 0.4 to 3.5% disodium phosphate by total weight of the third component; and with a weight ratio of phosphoric acid to disodium phosphate comprised from 1:1 to 10:1, preferably from 1:1 to 5:1;

wherein the buffering capacity of the buffer system is superior by a factor from 5 to 40 times than the buffer system of a conventional third component comprising about 0.1% of a buffering acidic compound being phosphoric acid and about 0.1% of a buffering alkali compound being disodium phosphate by total weight of the third component.

In a second aspect, the present invention relates to hair treating composition, said composition having a pH from 6.0 to 10.5 and comprising:

from 0.5% to 8% an oxidizing agent;
from 0.25% to 6% of an alkalizing agent;

wherein said composition is obtained from the mixing of an oxidizing component having an acidic pH from 1.5 and a tint component having a alkali pH from 7.5 to 11.5, said oxidizing component comprising a buffer system according to hair treating product as defined hereinbefore;

wherein the composition has a reduction of pH from 0.5 units, preferably from 0.5 to 6 units, more preferable from 0.5 to 4 units, versus a conventional oxidizing component as defined hereinbefore.

This hair treating composition is a ready-to-use composition, i.e. a composition ready to be applied immediately onto hair after its preparation.

In another aspect, the present invention relates to the use of an oxidizing component in a hair treating product as defined in claims 1 to 10, for cancelling the alkalinity of a tint component.

In another aspect, the present invention relates to an alkali cancelling oxidizing component, for use in a hair-treating product and/or for obtaining a hair treating composition upon mixing with a tint component, said oxidizing component having an acidic pH above 1.5 and comprising:

from 1% to 16% of at least one source of oxidizing agent by total weight of the oxidizing component; and a buffer system; said buffer system comprising:
a buffering acidic compound;
a buffering alkali compound;

wherein the buffering acidic compound is selected from the group consisting of organic and inorganic acids, and the corresponding buffering alkali compound is selected from the group consisting of alkali metal salts, amino acids, and salts thereof;

wherein the buffering acidic compound and the buffering alkali compound are present in amounts sufficient for providing a buffering effect equivalent to a buffer system comprising from 0.5% to 4% phosphoric acid and from 0.4 to 3.5% disodium phosphate by total weight of the oxidizing component; and with a weight ratio of phosphoric acid to disodium phosphate comprised from 1:1 to 10:1, preferably from 1:1 to 5:1; and wherein the buffering capacity of the buffer system is superior by a factor from 5 to 40 times than the buffer system of a conventional oxidizing component comprising about 0.1% of a buffering acidic compound being phosphoric acid and about 0.1% of a buffering alkali compound being disodium phosphate by total weight of the oxidizing component.

The hair treating product and the corresponding hair treating composition are particularly useful for colouring or bleaching hair. They are useful for providing permanent or demi-permanent coloration or bleaching to keratin fibers.

The present invention relies upon the provision of an oxidizing component, a tint component and optionally a third component; as well as a hair treating composition obtained by mixing the different components together. The provision of such types of components is customary into the field of hair treatment. However, the inventors have shown surprisingly that it would be particularly advantageous in providing an oxidizing component having specific properties, i.e. providing an oxidizing component acting as an alkali cancelling oxidizing component. By "akali cancelling oxidizing component", it is meant a hair treating composition into which up to 1.5% of alkalizing agent can be neutralized. Particularly, several advantages and benefits are associated with the present invention. Firstly, it allows obtaining an oxidizing component (as a premix) having a pH, which is not too low. Indeed, providing oxidizing component having a pH below 1.5, particularly below 2, requires special care. Such a low-pH can be harmful for both the hairdresser and the client, if not used appropriately. Using such low-pH oxidizing components is therefore not recommended, and could even be severely regulated, while it may be necessary to use them when there is the need of significantly reducing the pH of the tint component, upon mixing. Secondly, it allows obtaining an oxidizing component having a buffering effect over a large spectrum for buffering the pH of—or alkali cancelling—the tint component, upon mixing. Indeed, it may be obtained a hair treatment composition with a reduction of pH from 0.5 units, preferably from 0.5 to 6 units, more preferable from 0.5 to 4 units, versus a conventional hair treatment composition obtained from conventional oxidizing component comprising about 0.1% of a buffering acidic compound being phosphoric acid and about 0.1% of a buffering alkali compound being disodium phosphate by total weight of the oxidizing component. Thirdly, the present invention is suitable for use with conventional dyes and additional compounds added to hair treatment compositions. Fourthly, the present invention provides a great versatility to the oxidizing component, hence allowing using the same line-up of tint components, both for permanent or demi-permanent treatments, by merely using different oxidizing components. Fifthly, the present invention provides superior benefits particularly when the concentrations of the buffering acidic compound and the concentration of the buffering alkali compound—forming the buffer system present in the oxidizing component—are correlated with the concentration of the alkalizing agent present in the tint component; meaning that it is preferred to rely upon lower buffer concentrations for low alkali concentration, and higher buffer concentrations for high alkali concentration. Hence, the hairdresser or the user now only needs to rely upon one line-up of tint components, instead of at least two before, for achieving Level 2 and Level 3 colouration. This approach is not usual, as buffer systems—which are sometimes added to pre-mixes—are conventionally present at much lower levels e.g. about 25 to 40 times lower e.g. about 0.1% of a buffering acidic compound and about 0.1% of a buffering alkali compound by total weight of the oxidizing component. In commercialized hair colouring or bleaching products or compositions, it is sometimes added buffer systems, e.g. tetrasodium pyrophosphate/phosphoric acid or disodium phosphate/phosphoric acid, which are always added at very low levels, hence not providing the benefits and advantages of the present invention. For example, the applicant commercializes an oxidizing component for Level 3 colouration, under the tradename Illumina Japan Cream developer, which comprises respectively 0.08% disodium phosphate and 0.095% phosphoric acid. Such buffer systems, while contributing possibly to the stabilization of the system, where not usually influencing significantly the pH in the ready-to-use hair colouring or bleaching composition. Fifthly, the present invention allows obtaining oxiding components, and hair treating composition obtained therefrom, exhibiting equally good properties of mixing, application and odor as conventional techniques.

pH of the Oxidizing Component, the Tint Component, and the Hair Treating Composition Obtained Thereof The oxidizing component has an acidic pH above 1.5, preferably from 2, more preferably from 2 to 4, still more preferably from 2 to 3. Providing an oxidizing component with a pH below 2 may be necessary, while it is not recommended for safety reasons. Indeed, such oxidizing component may be harmful especially on skin if not used appropriately such as in a non-diluted form.

The tint component has an alkali pH from 7.5 to 11.5, preferably pH from 9 to 11.

The hair treating composition, obtaining upon mixing of the oxidizing component and the tint component, has a pH from 6.0 to 10.5, and exhibits a reduction of pH from 0.5 units, preferably from 0.5 to 6 units, more preferable from 0.5 to 4 units. This difference of pH between the tint component and the hair treating composition is particularly useful in that it allows obtaining an alkali cancelling effect, without noticeably impairing for the consumer the colouration or bleaching performance of the composition obtained.

Buffer System

The oxidizing component, or alternatively a third component, comprises a buffer system; said buffer system comprising a buffering acidic compound, and a buffering alkali compound.

The buffering acidic compound is selected from the group consisting of organic and inorganic acids; preferably from the group consisting of sulphurous acid, sulphuric acid, hydrochloric acid, hyponitrous acid, nitrous acid, nitric acid, phosphoric acid, phosphorous acid, citric acid, malic acid, and their mixtures; more preferably from the group consisting of phosphoric acid, phosphorous acid, citric acid, malic acid, hydrochloric acid, hyponitrous acid and their mixtures; still more preferably wherein the buffering acidic compound is phosphoric acid, hydrochloric acid, hyponitrous acid, and their mixtures; most preferably wherein the buffering acidic compound is phosphoric acid.

In one embodiment, the buffering acidic compound may be selected from the group consisting of organic and inorganic acids. In another embodiment, the buffering acidic compound may be an inorganic acid. In another embodiment, the buffering acidic compound may be an organic acid. The inorganic acids may be selected from the group consisting of sulphurous acid, sulphuric acid, hydrochloric acid, hyponitrous acid, nitrous acid, nitric acid, phosphoric acid, phosphorous acid, and mixtures thereof. The organic acids may be selected from the group consisting of citric acid, malic acid, and mixtures thereof.

The corresponding buffering alkali compound is selected from the group consisting of alkali metal salts, amino acids, and salts thereof; preferably from the group consisting of glycine, alkali metal salts, amino acids, chlorides, nitrates and salts thereof; more preferably alkali metals of chlorides, nitrates and/or phosphoric acid, glycine and salts thereof; still more preferably alkali metals of phosphoric acid and salts thereof most preferably disodium phosphate and potassium chloride. Alkali metals of phosphoric acid ($H_3PO_4$) may be selected from the group consisting of potassium dihydrogen phosphate ($KH_2PO_4$), sodium dihydrogen phosphate ($NaH_2PO_4$), dipotassium hydrogen phosphate ($K_2HPO_4$), disodium hydrogen phosphate ($Na_2HPO_4$), potassium phosphate ($K_3PO_4$), sodium phosphate ($Na_3PO_4$) and mixtures thereof.

The combination of the buffering acidic compound and its buffering alkali compound may be selected from the group consisting of phosphoric acid/potassium dihydrogen phosphate, phosphoric acid/sodium dihydrogen phosphate, phosphoric acid/dipotassium hydrogen phosphate, phosphoric acid/disodium hydrogen phosphate, phosphoric acid/potassium phosphate, phosphoric acid/sodium phosphate, hydrochloric acid/potassium chloride, hydrochloric acid/potassium hydrogen phthalate, hydrochloric acid/sodium citrate, hydrochloric acid/potassium dihydrogen citrate, citric acid/dihydrogen citrate, citric acid/sodium citrate or citric acid/disodium hydrogen phosphate.

In a preferred embodiment, the buffer system comprises a buffering acidic compound being phosphoric acid, and a corresponding buffering alkali compound being disodium phosphate. Alternatively, the buffer system comprises a buffering acidic compound being phosphoric acid, and a corresponding buffering alkali compound being glycine; or a buffering acidic compound being citric acid, and a corresponding buffering alkali compound being disodium phosphate; or a buffering acidic compound being citric acid, and a corresponding buffering alkali compound being glycine.

The buffering acidic compound and the buffering alkali compound are present in amounts sufficient for providing a buffering effect of reference. The buffering effect of reference is equivalent to a buffer system comprising from 0.5% to 4% phosphoric acid and from 0.4 to 3.5% disodium phosphate by total weight of the oxidizing component in a weight ratio of phosphoric acid to disodium phosphate comprised from 1:1 to 10:1; preferably from 1:1 to 5:1; more preferably from 1:2 to 1:1. While the preferred buffer system comprises a buffering acidic compound being phosphoric acid, and a corresponding buffering alkali compound being disodium phosphate, any alternative buffer system may be used, as far as it provides an equivalent buffering effect as the buffer system of reference. The amount alternative buffering acidic compound may be calculated versus the amount of phosphoric acid. The amount of the alternative buffering alkali compound may be calculated versus the amount of disodium phosphate.

The buffering effect may be equivalent to a buffer system of reference comprising:
from 0.5% to 4%, preferably from 1% to 3.5%, more preferably from 1.5% to 3%, phosphoric acid, by total weight of the oxidizing component;
from 0.4 to 3.5%, preferably 0.5% to 3%, more preferably from 0.8% to 2%, disodium phosphate, by total weight of the oxidizing component;
a weight ratio of phosphoric acid to disodium phosphate comprising from 1:1 to 10:1, preferably from 1:1 to 5:1, more preferably from 1:2 to 1:1.
Alternatively, the buffering effect may be equivalent to a buffer system of reference comprising:
from 0.5% to 4% phosphoric acid, by total weight of the oxidizing component;
from 0.3% to 4% disodium phosphate, by total weight of the oxidizing component;
a weight ratio of phosphoric acid to disodium phosphate comprising from 1:1 to 10:1.

When the buffering acidic compound is phosphoric acid, the oxidizing component may comprise from 0.5% to 4%, preferably from 1% to 3.5%, more preferably from 1.5% to 3%, of buffering acidic compound by total weight of the oxidizing component; for example about 3%. When the buffering alkali compound is disodium phosphate (or alternatively glycine), the oxidizing component may comprise from 0.4 to 3.5%, preferably from 0.5% to 3%, more preferably from 0.8% to 2%, of buffering alkali compound by total weight of the oxidizing component; for example about 2%. In contrast, conventional buffer systems present in oxidizing components usually comprises less than 0.1% of buffering acidic compound, and less than 0.1% of buffering alkali compound, by total weight of the oxidizing component.

In one embodiment, the product may comprise:
(1) an oxidizing component having an acidic pH above 1.5 and comprising:
from 1% to 16% of at least one source of oxidizing agent by total weight of the oxidizing component;
a buffer system; said buffer system comprising a buffering acidic compound and a buffering alkali compound;
wherein the buffering acidic compound is phosphoric acid;
wherein the corresponding buffering alkali compound is an alkali metal of phosphoric acid, preferably wherein the corresponding buffering alkali compound is selected from the group consisting of potassium dihydrogen phosphate, sodium dihydrogen phosphate, dipotassium hydrogen phosphate, disodium hydrogen phosphate, potassium phosphate, sodium phosphate and mixtures thereof;
wherein the oxidizing component comprises from 0.5% to 4%, preferably from 1% to 3.5%, more preferably from 1.5% to 3%, of buffering acidic compound by total weight of the oxidizing component;
wherein the oxidizing component comprises from 0.4 to 3.5%, preferably from 0.5% to 3%, more preferably from 0.8% to 2%, of buffering alkali compound by total weight of the oxidizing component
wherein the weight ratio of phosphoric acid to the alkali metal of phosphoric acid is comprised from 1:1 to 10:1, preferably from 1:1 to 5:1;
(2) a tint component having an alkali pH from 7.5 to 11.5, and comprising from 0.5% to 12% of at least one source of alkalizing agent by total weight of the tint component; and
wherein the oxidizing and/or tint components are optionally substantially free of a source of carbonate ions, carbamate ions, hydrogen carbonate ions, and mixtures thereof.

This buffer system has particularly the advantage of lowering significantly the pH in the ready-to-use colouring or bleaching composition, so that to achieve an alkali/ammonia cancelling effect, while allowing providing a safe oxidizing component not having an extreme acidic pH, and while allowing using only one line-up of tint components for achieving both permanent and demi-permanent colouring or bleaching.

In an alternative, less preferred embodiment, the buffering system may be provided in a third component, different from the oxidizing component and the tint component. The third component may be mixed first with the oxidizing component, for obtaining an oxidizing component with a buffering system, prior mixing with the tint component. The third component may also be mixed concomitantly with the oxidizing component and the tint component.

Oxidizing Agent

The oxidizing component, according to the present invention, further comprises at least one source of an oxidizing agent. Any oxidizing agent known in the art may be used. Preferred oxidizing agents are water-soluble peroxygen oxidizing agents. As used herein, "water-soluble" means that in standard conditions at least about 0.1g, preferably about 1g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

The oxidizing component comprises from 1% to 16%, preferably from 1% to 15%, more preferably from 1.5% to 12%, of at least one source of oxidizing agents by weight of the total oxidizing component.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In one embodiment, the oxidizing component comprises a water-soluble oxidizing agent selected from the group consisting of hydrogen peroxide, percarbonates (which may be used to provide a source of both oxidizing agent and carbonate ions and or ammonium ions), persulphates, and mixtures thereof.

In one embodiment, the oxidizing component comprises a water-soluble oxidizing agent being hydrogen peroxide.

In one embodiment, the oxidizing component is substantially free of a source of alkalizing agent as described herewith, including ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal hydroxides (such as sodium hydroxides) and ammonium hydroxides; alkali metal and ammonium carbonates; and mixtures thereof. Particularly, the oxidizing component is substantially free of alkali metal and ammonium carbonates.

Alkalizing Agents

The tint component, according to the present invention, comprises a source of alkalizing agent. Any alkalizing agent known in the art may be used.

The tint component comprises from 0.5% to 12%, alternatively from 0.5% to 6%, preferably from 0.5% to 5%, more preferably from 0.75% to 3%, of a source of alkalizing agent, by weight of the total tint component.

Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal hydroxides (such as sodium hydroxides) and ammonium hydroxides; alkali metal and ammonium carbonates; and mixtures thereof. Typical alkalizing agents are ammonia and/or monoethanolamine. Preferably, if present, the ammonium ions and carbonate ions are present in the composition at a weight ratio of from 3:1 to 1:10, alternatively from 2:1 to 1:5.

In one embodiment, the alkalizing agent is not selected from the group consisting of any carbonate ion sources, including alkali metal and ammonium carbonates. Suitable alkalizing agents may be selected from the group consisting of ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal hydroxides (such as sodium hydroxides) and ammonium hydroxides; and mixtures thereof.

Mixing Prior Application

The oxidizing component and the tint component, which are premixes, aim at being mixed together shortly prior application onto hair. Both components may be mixed from 1 mn to 30 mn, preferably 1 mn to 15 mn, more preferably 1 mn to 5 mn prior application onto keratin fibers. Upon mixing, it is obtained a ready-to-use hair treatment composition.

Kits or Multi-Choice Products

The hair-treating product comprises an oxidizing component, a tint component, and optionally a third component.

The components can be individually packaged, and be provided as a kit (or box). The provision of kits is particularly useful for retail business, such kits being commercialized to the consumer wishing to treat his/her hair by him/herself either in salons or in supermarkets. The oxidizing component, the tint component and optionally the third component are therefore sold together, for obtaining one type of treatment. They are usually single-use kits.

The components can also be individually packaged, without being provided as a kit, but instead multi-choice products. The provision of multi-choice products is particularly useful for salon business, such multi-choice products being used by the hairdresser. The oxidizing component, the tint component and optionally the third component are therefore sold separately. The hair dresser would have therefore the possibility to choose both the oxidizing component, the tint component, and optionally the third component needed, depending on the hair type of the clients, the treatment (colouring or bleaching) expected, etc.

Other Ingredients

The oxidizing component and/or the tint component, according to the present invention, may comprise, in addition to the ingredients indicated above, further ingredients in order to further enhance the properties of the composition, as long as these are not excluded by the claims.

Suitable further ingredients include, but not limited to: solvents; oxidative dye precursors, direct dyes; chelants; radical scavengers; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Alternatively, the further ingredients are not selected from the group consisting of carbonate ion sources, peroxymonocarbonate ion sources, and mixtures thereof, so that the further ingredients include, but not limited to: solvents; oxidative dye precursors, direct dyes; chelants; radical scavengers; thickeners and/or rheology modifiers; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The oxidizing component and/or the tint component, or the hair treating composition obtained thereof, may further comprise a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In one embodiment, the solvent may be selected from the group consisting of water, ethanol, propanol, isopropanol, glycerol, 1,2-propylene glycol, hexylene glycol, ethoxy diglycol, and mixtures thereof.

The oxidizing component and/or the tint component may comprise water as a main ingredient, particularly in a total amount ranging from at least about 60% to 97%, preferably from 70% to 96.5%, more preferably from 75% to 96.5% by weight of the total component. Typically, when present, the oxidizing component and/or the tint component comprises a total amount of organic solvents ranging from about 1% to about 20%, by weight of the total component.

The hair treating composition may comprise water as a main ingredient, particularly in a total amount ranging from at least about 50%, alternatively from at least about 60%, alternatively from at least about 70%, by weight of the total hair treating composition. When present, the hair treating composition may comprise a total amount of organic solvents ranging from about 0.5% to about 20%, by weight of the total hair treating composition.

Oxidative Dye Precursors

The tint component, or the hair treating composition obtained thereof, may further comprise oxidative dye precursors, which are usually classified either as primary intermediates (also known as developers) or couplers (also known as secondary intermediates). Various couplers may be used with primary intermediates in order to obtain different shades. Oxidative dye precursors may be free bases or the cosmetically acceptable salts thereof. The tint component may comprise a total amount of oxidative dye precursors ranging up to about 14%, preferably from about 0.005% to about 12%, more preferably from about 0.005% to about 10%, by weight of the total tint component.

The hair treating composition may comprise a total amount of oxidative dye precursors ranging up to about 7%, alternatively from about 0.0025% to about 6%, alternatively from about 0.0025% to about 5%, by weight of the total hair treating composition.

Suitable primary intermediates include, but are not limited to: toluene-2,5-diamine, p-phenylenedi amine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a] pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo1,5-a]pyridin-2-yl) oxylethanol hydrochloride, salts thereof and mixtures thereof.

Suitable couplers include, but are not limited to: resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis (azanediyl)diethanol, benzene-1,3-diamine, 2,2'-(4,6-diamino-1,3-phenylene)bis(oxy)diethanol, 3-(pyrrolidin-1-yl-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxo1-5-ylamino)ethanol (also known as hydroxyethyl-3,4-methylenedioxyaniline), and mixtures thereof.

Direct Dyes

The tint component, or the hair treating composition obtained thereof, may further comprise compatible direct dyes, in an amount sufficient to provide additional coloring, particularly with regard to intensity.

The tint component may comprise a total amount of direct dyes ranging from about 0.001% to about 4%, by weight of the total tint component.

The hair treating composition may comprise a total amount of direct dyes ranging from about 0.0005% to about 2%, by weight of the total hair treating composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No.2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No.1, HC Blue No. 14; Natural dyes such as Annato, Anthocyanin, Beetroot, Carotene, Capsanthin, Lycopene, Chlorophyll, Henna, Indigo, Cochineal; and mixtures thereof.

All developers, couplers and direct dyes can be used, as far as they are physiologically acceptable and that they do not have influence on the buffering effect.

Chelants

The oxidizing and/or the tint component, or the hair treating composition obtained thereof, may further comprise chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference. A chelant is usually present in the oxidizing component for stability reason.

The oxidizing component and/or the tint component may comprise a total amount of chelants ranging from at least about 0.01%, preferably from about 0.01% to about 4%, more preferably from about 0.01% to about 1.5%, by weight of the total component.

The hair treating composition may comprise a total amount of chelants ranging from at least about 0.01%, alternatively from about 0.02% to about 4%, alternatively from about 0.02% to about 3%, alternatively from about 0.02% to about 2%, by weight of the total hair treating composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof alternatively sodium salts, potassium salts, ammonium salts, and mixtures thereof alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: Hydroxyethylethylendiaminetriacetic acid (HEDTA), diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), ethylenedicysteic acid (EDC), ethylenediamine-N-N'-bis(ortho-hydroxyphenyl acetic acid) (EDDHA), diaminoalkyldi(sulfosuccinic acids) (DDS), N,N'-bis(2-hydroxybenzyl) ethylenediamine-N,N'-diacetic acid (HBED), their salts thereof, and mixtures thereof. Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative—$PO_3R_2$, wherein $R_2$ is a $C_1$ to $C_6$ alkyl or aryl radical and salts thereof.

Suitable aminophosphonic acid chelants include, but are not limited to: aminotri-(1-ethylphosphonic acid), ethylenediaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylene-diamine-tetra-(methylenephosphonic acid) (EDTMP) and diethylene-triamine-penta-(methylenephosphonic acid) (DTPMP), their salts thereof, their derivatives thereof, and mixtures thereof. Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

Radical Scavengers

The oxidizing agent and/or the tint component, or the hair treating composition obtained thereof, may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring bleaching process.

The oxidizing and/or the tint component may comprise a total amount of radical scavengers ranging from about 0.2% to about 20%, preferably from about 2% to about 14%, by weight of the total component.

The composition may comprise a total amount of radical scavengers ranging from about 0.1% to about 10%, alternatively from about 1% by weight to about 7%, by weight of the total hair treating composition.

Suitable radical scavengers include, but are not limited to: alkanolamines, amino sugars, amino acids, esters of amino acids, and mixtures thereof alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The tint component described herein may further comprise, in addition to the source of alkalizing agent discussed above, a pH modifier and/or buffering agent in an amount that is sufficiently effective to adjust the pH of the tint component to fall within a range from 8 to 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

In one embodiment, pH modifiers and/or buffering agents are not selected from the group consisting of alkali metal and ammonium hydroxides and carbonates, and mixtures thereof.

Thickeners and/or Rheology Modifiers

The oxidizing and/or tint component, or the hair treating composition obtained thereof, may further comprise a thickener in an amount sufficient to provide the composition with a viscosity so that it can be readily applied to the hair without unduly dripping off the hair and causing mess.

The oxidizing and/or the tint component may comprise a total amount of thickeners ranging from at least about 0.1%, alternatively at least about 0.15%, by weight of the total component.

The hair treating composition may comprise a total amount of thickeners ranging from at least about 0.05%, alternatively at least about 0.3%, by weight of the total hair treating composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules. Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below $$CH2\!=\!C(R1)CH_2OBnR \tag{I}$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (II) below $$CH2\!=\!C(R1)COOH \tag{II}$$

in which R1 is chosen from H, CH3, C2H$_5$ and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (III) below $$CH2\!=\!C(R1)COOBnR2 \tag{III}$$

in which R1 is chosen from H, CH$_3$, C2H$_5$ and CH$_2$COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (IV) below $$CH2\!=\!C\!< \tag{IV}$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch. Other preferred associative polymers include polyether polyurethane, commercially available as Aculyn-44/-46 by Rohm and Haas. Further preferred associative polymers include cellulose modified with groups comprising at least one C8—C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacantha, ghatti gums, karaya gums, carob gums, galactomannans, such as guar gums, and nonionic derivatives thereof (hydroxypropyl guar) and bio-polysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums—Polysaccharides and their Derivatives", edited by Roy L. Whistler, Second Edition, published by Academic Press Inc., all three being incorporated herein by reference. A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrrolidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates / Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth—10 phosphate, Di-cetyl phosphate and Cetearyl alcohol (available as Crodafos CES), and mixtures thereof.

Carbonate Ion Sources

The oxidizing and/or tint component, or the hair treating composition obtained thereof, may further comprise a source of carbonate ions, carbamate ions, hydrogen carbonate ions, and mixtures thereof in a sufficient amount to reduce damage to the hair during the coloring process.

The oxidizing and/or tint component may comprise a total amount of a carbonate ion source ranging from about 0.1% to about 30%, preferably from about 0.1% to about 10%, more preferably from about 1% to 7%, by weight of the total component.

The hair treating composition may comprise a total amount of a carbonate ion source ranging from about 0.1% to about 15%, alternatively from about 0.1% to about 10%, alternatively from about 1% to about 7%, by weight of the total hair treating composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof alternatively sodium hydrogen carbonate, potassium hydrogen carbonate, and mixtures thereof alternatively ammonium carbonate, ammonium hydrogen carbonate, and mixtures thereof.

Alternatively, the oxidizing and/or tint component, or the hair treating composition obtained thereof, may be substantially free of a source of carbonate ions, carbamate ions, hydrogen carbonate ions, and mixtures thereof.

Conditioning Agents

The oxidizing and/or tint component, or the hair treating composition obtained thereof, may further comprise a conditioning agent, and/or be used in combination with a composition comprising a conditioning agent.

If present in the oxidizing and/or the tint component, any of these components may comprise a total amount of conditioning agents ranging from about 0.01% to about 20%, preferably from about 0.1% to about 15%, more preferably from about 0.2% to about 10%, by weight of the total component.

The hair treating composition may comprise a total amount of conditioning agents ranging from about 0.01% to about 20%, preferably from about 0.1% to about 15%, more preferably from about 0.2% to about 10%, still more preferably from about 0.2% to about 2%, even more preferably from about 0.5% to 2%, by weight of the total hair treating composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion. Suitable silicones also include: silicones containing groups that may be ionized into cationic groups, for example aminosilicones containing at least 10 repeating siloxane $(Si(CH_3)_2—O)$ units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si—O$, $R_{12}(CH_3)_2Si—O$, where $R_{12}$ can be either OH or $OR_{13}$, where $R_{13}$ is a C1-C8 alkyl group, or a mixture of both terminal groups. These silicones are also available as preformed emulsions. Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones. Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5\times10^6$, alternatively from about 1000 to about $3\times10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); coplolymers of vinyl pyrrolidone and dialkyaminoalkyl acrylates or methactylates, including polymers known as Polquaternium-11 (see Gafquat 440/734/755/755N by ISP; Luviquat PQ11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquaternium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquaternium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquaternium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch; Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clamant; Mackernium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF; Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/ Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)–A1–N+(R3)(R4)–B1–][2X–], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5—D and —CO—NH—R5—D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X– is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is $(CH_2)_3$ and B1 is $(CH_2)_6$ and X=Cl; as polyquaternium-34 where R1 and R2 are ethyl radicals and R3 and R4 are methyl radicals and A1 is $(CH_2)3$ and B1 is $(CH_2)3$ and X=Br (e.g. Mexomere PAX by Chimax).

7) Polyquaternary ammonium polymers comprising repeating units of formula [–N+(R6)(R7)–(CH$_2$)r–NH–CO—(CH$_2$)q-(CO)t-NH—(CH$_2$)s-N+(R8)(R9)-A-][2X–], in which R6, R7, R8 and R9 which may be identical or different, are chosen from a hydrogen atom and a methyl, ethyl, propyl, hydroxyethyl, hydroxypropyl, and —CH$_2$CH$_2$ (OCH$_2$CH$_2$)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X– is anion such as a halide. T is an integer chosen to be equal to 0 or 1. A is chosen from divalent radicals such as —CH2—CH2—O—CH2—CH2—. Suitable examples include: polymers known as polyquaternium-2, where r=s=3, q=0,t=0, R6, R7, R8 and R9 are methyl groups, and A is —CH2—CH2—O—CH2—CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2—CH2—O—CH2—CH2; as Polyquaternium 18, where r=s=3, q=7, t=1 R6, R7, R8 and R9 are methyl groups, and A is —CH2—CH2—O—CH2—CH2; as the block copolymer formed by the reaction of Polyquaternium-2 with Polyquaternium-17, which are known as Polyquatemium 27 (e.g. Mirapol 175 by Rhodia).

8) Copolymers of vinylpyrrolidones and of vinylimidazoles and optionally vinylcaprolactums, including polymers known as Poly quaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquatemary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen CN/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquatemium 51 (e.g. Lipidure-PMB by NOF), as Polyquaternium 54 (e.g. Qualty-Hy by Mitsui), as Polyquaternium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)$_2$)—R11—(Si(CH3)2—O)x—R11—(N+(CH$_3$)$_2$)—R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane —(Si(CH$_3$)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH$_3$)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane —(Si(CH3)2—O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In a preferred embodiment, the cationic polymer is selected from the group consisting of polyquaternium 37, polyquaternium 7, polyquaternium 22, polyquaternium 87, and mixtures thereof; particularly from the group consisting of polyquaternium 37, polyquaternium 22, and mixtures thereof.

Surfactants

The oxidizing and/or tint component, or the hair treating composition obtained thereof, may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

The oxidizing and/or tint component may comprise a total amount of surfactants ranging from about 0.7% to about 60%, preferably from about 1% to about 30%, more preferably from about 1.5% to about 20%, by weight of the total component.

The hair treating composition may comprise a total amount of surfactants ranging from about 1% to about 60%, alternatively from about 2% to about 30%, alternatively from about 3% to about 20%, by weight of the total hair treating composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

Nonionic surfactants are compounds that are well known (see, for example, in this respect "Handbook of Surfactants" by M. R. Porter, published by Blackie & Son (Glasgow and London), 1991, pp. 116-178). Suitable non-ionic surfactants include, but are not limited to: polyethoxylated, polypropoxylated and polyglycerolated fatty acids, alkyl phenols, a-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CON HCH$_2$CH$_2$—N$^+$($R_3$)($R_4$)(CH$_2$COO$^-$), (VI) in which: $R_2$ is chosen from alkyl radicals derived from an acid $R_2$—COOH present in hydrolysed coconut oil, and heptyl, nonyl and undecyl radicals, $R_3$ is a O-hydroxyethyl group and $R_4$ is a carboxymethyl group; and of $R_5$—CONHCH$_2$CH$_2$—N(B)(C) (VII) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (VIII) below:

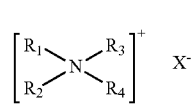

(VIII)

wherein X$^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein Ri to R4 are as below in i) or ii). i) Radicals Ri to R3, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from $(C_{12}-C_{22})$alkylamido$(C_2-C_6)$alkyl and $(C_{12}-C_{22})$ alkylacetate radicals. A suitable cationic surfactant is, for example, a dicetyldimethyl ammonium salt (for example chloride);

B) Quaternary ammonium salts of imidazolinium of formula (IX) below:

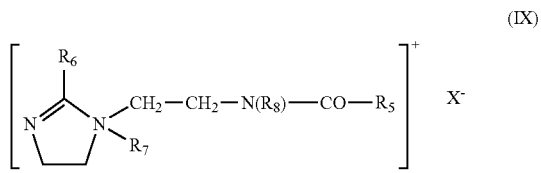

in which R5 is chosen from alkenyl and alkyl radicals comprising from 8 to 30 carbon atoms, for example fatty acid derivatives of tallow, R6 is chosen from a hydrogen atom, $C_1-C_4$ alkyl radicals and alkenyl and alkyl radicals comprising from 8 to 30 carbon atoms, R7 is chosen from $C_1-C_4$ alkyl radicals, $R_8$ is chosen from a hydrogen atom and $C_1-C_4$ alkyl radicals, and $X^-$ is an anion chosen from halides, phosphates, acetates, lactates, alkyl sulphates, alkyl sulphonates and alkylaryl sulphonates. In one embodiment, R5 and R6 are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quatemium-83 (CTFA 1997), commercially available as "Rewoquat®" W75/W90/W75PG/W75HPG by Witco.

C) Diquaternary ammonium salts of formula (X):

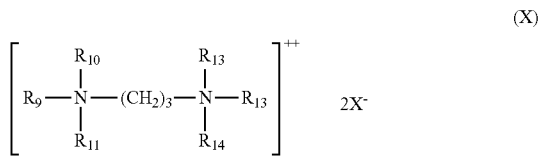

in which R9 is chosen from aliphatic radicals comprising from about 16 to 30 carbon atoms, Rio, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallow-diammonium dichloride.

D) Quaternary ammonium salts comprising at least one ester function, of formula (XI) below:

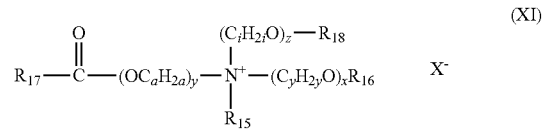

in which: R15 is chosen from C1-C6 alkyl radicals and C1-C6 hydroxyalkyl and dihydroxyalkyl radicals; R16 is chosen from: a radical R19C(0)-, linear and branched, saturated and unsaturated C1-C22 hydrocarbon-based radicals R20, and a hydrogen atom, R18 is chosen from: a radical R21C(0)-, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X– is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XI) can be used, in which: R15 is chosen from methyl and ethyl radicals, x and y are equal to 1; z is equal to 0 or 1; n, p and r are equal to 2; R16 is chosen from: a radical R19C(0)-, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Method of Use/Kits

It is understood that the examples of methods of use and embodiments described herein are for illustrative purposes only and that various modifications or changes in light thereof will be suggested to one skilled in the art without departing from the scope of the present invention.

Retail oxidative hair dye compositions are usually sold in kits comprising, in individually packaged components such as separate containers, a dye component (also called "dye cream" for emulsions or "dye liquid" for solutions) comprising the oxidative dye precursors and alkalizing agent which is typically ammonia in a suitable carrier and; a oxidizing component (also called "hydrogen peroxide cream" for emulsions or "hydrogen peroxide liquid" for solutions) comprising the oxidizing agent (usually hydrogen peroxide). The consumer mixes the dye component and oxidizing component together immediately before use and applies it onto the hair. Similarly, retail bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

For, the professional hair salon market, the hair dye component and the oxidizing component and/or bleaching compositions are typically supplied independently to allow the professional to select a preferred combination.

After working the combined mixture for a few minutes (to insure uniform application to all of the hair), the oxidative dye composition is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original colour to the desired colour.

In both retail and professional applications, an optional conditioning agent can also be provided. In this embodiment, all three compositions can be mixed immediately before use and applied together, or the conditioning agent can be applied (after an optional rinse step), as a post-treatment immediately after the oxidative dye composition or bleaching composition resulting from the mixture of the other containers.

The kits may also comprise as optional components a pre-treatment composition and/or a colour refresher composition. Such colour refresher compositions comprise at least one pre-formed dye and may be applied to the hair immediately after the oxidative colour i.e. from about 1 minute after oxidative hair dye or bleach application to about 60 days after the application. These colour refresher composition can be used to increase the initial colour obtained and or boost the colour during the wash and style cycle until the next oxidative colouring or bleaching event.

Methods of Manufacture

The kits described hereinabove are well-known in the art and the compositions in each container can be manufactured utilizing any one of the standard approaches, these include a) Oil-in-water' process, b) 'Phase Inversion' process and c) 'One-pot' process. For example, when using "oil-in-water" process, surfactants of the present invention are added to approximately 50% of total water amount of the composition at about 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

Packaging and dispensing devices The present invention may be provided in a variety of packaging devices and/or dispensing devices. These dispensing devices can come in the form of separate devices, which may be used independently, or in combination with one another. Typically, the hair colouring or bleaching compositions are contained within separate single or multi compartment containers so that the compositions can be stored separately from one another before use. The compositions are then mixed together by a mixing means and then dispensed from the device and applied to the consumer's hair by an application means.

The most common packaging device which can be used for the present invention involves storing the oxidizing component in a container such as a bottle, tube, aerosol, or a sachet and separately storing the dye lotion in an additional compartment within the oxidizing container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the oxidizing component and the dye component by any means. This may simply involve the use of a mixing bowl into which the compositions are dispensed and then mixed, preferably using a mixing means such as a tool.

Alternatively, it may involve the addition of one of the compositions into the container of the other composition (typically the dye composition is added to the oxidizing composition), followed by manual shaking or mixing with a tool. Another system involves the perforation or displacement of a seal located between the separate compartments of the dye and oxidizing composition within a single container or sachet followed by manual mixing within the container or in a separate and or additional container.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it may be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined /selected hair strands may also be used.

Additional device technology can be used to assist in the penetration of the product into the hair. Examples of such technology include heating devices, ultraviolet light devices and ultrasound devices.

Method of Hair Dyeing

The hair treating composition may be obtained by mixing immediately prior to use a tint component and an oxidizing component. A sufficient amount of the mixture is applied to the hair, according to the hair abundance, generally from about 60 to about 250 grams. Upon such preparation the composition is applied to the hair to be dyed and remains in contact with the hair for an amount of time effective to dye the hair. Typically, the hair treating composition is allowed to act on the hair from about 2 to about 60, preferably about 15 to about 45, more preferably about 30 minutes, at a temperature ranging from 15° C. to about 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The method of treating hair with the composition may therefore comprise the steps of:

(i) providing a tint component, preferably comprising the gel network thickening system, and if present an alkalizing agent and oxidative precursor dyes and/or direct dyes;

(ii) providing an oxidizing component comprising an oxidizing agent;

(iii) mixing the oxidizing component with the tint component to obtain a hair treating composition according to the invention;

(iv) applying the composition obtained for bleaching or oxidative dyeing of keratin fibers onto the hair.

The glycerol can be comprised in the tint component or the oxidizing component or distributed in both components. Typically glycerol will be at least comprised in the dye composition to serve as solvent for the dyes.

The method may further comprise waiting a period of time, typically between 2 minutes and 60 minutes, and then rinsing the hair treating composition from the hair. The hair treating composition can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse. The composition may be dispensed as a solid form to which water is added to generate the oxidant and form a thickened vehicle suitable for hair coloring.

Methods of Making—Kit

The tint component or oxidizing component, and the corresponding hair treating (colouring or bleaching) compositions, may be manufactured by conventional processes known in the art for manufacturing oxidative dyeing products, and admixing the ingredients of each component/composition in suitable vessels, followed by packaging in appropriate individual containers. The components may be for example packaged in plastic or aluminium bottles.

In particular, the present invention may be provided as a kit comprising different components to be mixed by the consumer or salon stylist to obtain a hair dyeing composition according to the invention. Such a kit may comprise a tint component and a oxidizing component as indicated above.

The kit may be presented in a single package comprising separate containers for the tint component, the oxidizing component, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair colouring or bleaching hair composition for one use.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

Formulations

The oxidizing and the tint components are aqueous compositions.

Oxidizing components O1 and O2, as disclosed below, have the same formulation, except for the proportion in $H_{2O_2}$ and the buffer system (qsp 100% water by weight of the total component). Tint components T1 to T6 also have the same formulations, except for the proportion in $NH_3$ and in ammonium sulphate, if present (qsp 100% water by weight of a total composition).

pH

The pH of the components and compositions may be measured using any suitable method and pH meter e.g. portable pH meters FiveGo™ from Mettler Toledo. A two-point calibration of the pH meter is recommended for example by using buffer solutions of known pH such as the buffer solutions of pH 4.01, pH 7.0 and pH 10.0.

Buffer Systems

The following buffer systems have been tested:

BF (comparative)–0.08% disodium phosphate+0.095% phosphoric acid (comparative);

Buffer system BF1–0.4% disodium phosphate+0.5% phosphoric acid;

Buffer system BF2–0.5% disodium phosphate+0.75% phosphoric acid;

Buffer system BF3–1% disodium phosphate+1.5% phosphoric acid;

Buffer system BF4–1.5% disodium phosphate+3% phosphoric acid; and

Buffer system BF5–2% disodium phosphate+3% phosphoric acid.

Oxidizing Components

The buffer systems are added in an oxidizing component (base chassis) as follows:

Oxidizing component O1–2% $H_2O_2$+buffer system; and
Oxidizing component O2–12% $H_2O_2$+buffer system.

The tested oxidizing components have the following pH:

O1+BF (comparative)–pH=2.23;
O2+BF (comparative)–pH=2.13;
O1+BF1–pH=2.32;
O2+BF1–pH=2.04;
O1+BF2–pH=2.12;
O2+BF2–pH=1.91;
O1+BF3–pH=2.27;
O2+BF3–pH=1.95;
O1+BF4–pH=1.67;
O2+BF4–pH=1.57;
O1+BF5–pH=2.25; and,
O2+BF5–pH=1.94.

Tint Components

The following tint components have been tested:

Tint component T1–0.75%$NH_3$, pH=12;
Tint component T2–1.63% $NH_3$+0.5% ammonium sulphate, pH=10,68;
Tint component T3–2.50% $NH_3$ (25%)+1% ammonium sulphate, pH=10,86;
Tint component T4–3,75%$NH_3$+1% ammonium sulphate, pH=10,84;
Tint component T5–4.88% $NH_3$+1.5% ammonium sulphate, pH=10,73; and
Tint component T6–0.25% $NH_3$+5% ammonium sulphate+0.5% citric acid, pH=8,65.

Tests—Alkali Cancelling Effect

Tint components have been tested with the oxidizing components O1 comprising one of the buffer systems above at a weight ratio 1:1.

The pH of the resulting hair treating composition has been measured (first value), the pH drop versus the tint component has been calculated (second value), and then the difference in pH drop between the oxidizing components (invention) and the oxidizing component (reference) has been determined (third value).

| Demi proposition | |
|---|---|
| Mix 1:1 | T6 |
| O1(BFref) | 7.9 |
|  | −0.75 |
| O1(BF1) | 6.16 |
|  | −2.49 |
|  | Δ 1.74 |
| O1(BFref) | 7.9 |
|  | −0.75 |
| O1(BF2) | 5.56 |
|  | −3.09 |
|  | Δ 2.34 |

| Mix 1:1 | T1 |
|---|---|
| O1(BFref) | 10.18 |
|  | −1.51 |
| O1(BF3) | 9.22 |
|  | −2.47 |
|  | Δ 0.96 |

| Mix 1:1 | T1 | T2 |
|---|---|---|
| O1(BFref) | 10.18 | 10.24 |
|  | −1.51 | −0.49 |
| O1(BF4) | 6.62 | 9.41 |
|  | −5.07 | −1.32 |
|  | Δ 3.56 | Δ 0.83 |
| O1(BFref) | 10.18 | 10.24 |
|  | −1.51 | −0.49 |
| O1(BF5) | 6.95 | 9.42 |
|  | −4.74 | −1.31 |
|  | Δ 3.23 | Δ 0.82 |

| Permanent proposition | |
|---|---|
| Mix 1:1 | T1 |
| O1(BFref) | 10.18 |
|  | −1.51 |
| O1(BF3) | 9.22 |
|  | −2.47 |
|  | Δ 0.96 |

| Mix 1:1 | T1 | T2 | T3 |
|---|---|---|---|
| O1(BFref) | 10.18 | 10.24 | 10.29 |
|  | −1.51 | −0.49 | −0.39 |
| O1(BF4) | 6.62 | 9.41 | 9.75 |
|  | −5.07 | −1.32 | −0.93 |
|  | Δ 3.56 | Δ 0.83 | Δ 0.54 |
| O1(BFref) | 10.18 | 10.24 | 10.29 |
|  | −1.51 | −0.49 | −0.39 |
| O1(BF5) | 6.95 | 9.42 | 9.75 |
|  | −4.74 | −1.31 | −0.93 |
|  | Δ 3.23 | Δ 0.82 | Δ 0.54 |

Tint components have been tested with the oxidizing components O1 comprising one of the buffer systems BF at a weight ratio 1:2.

| Permanent proposition - Mix weight ratio 1:2 | | |
|---|---|---|
| Mix 1:2 | T4 | T5 |
| O1(BFref) | 10.25 | 10.31 |
|  | −0.61 | −0.53 |
| O1(BF4) | 9.54 | 9.76 |
|  | −1.30 | −1.08 |

-continued

| Permanent proposition - Mix weight ratio 1:2 | | |
|---|---|---|
| Mix 1:2 | T4 | T5 |
|  | Δ 0.69 | Δ 0.55 |
| O1(BFref) | 10.25 | 10.31 |
|  | −0.61 | −0.53 |
| O1(BF5) | 9.53 | 9.75 |
|  | −1.33 | −1.09 |
|  | Δ 0.72 | Δ 0.56 |

Each tint component T1 to T6 has been tested with the oxidizing components O1 comprising any one of the buffer systems BF (comparative), BF 1 to BF 5 at a weight ratio 1:3.

| Permanent proposition - Mix weight ratio 1:3 | | |
|---|---|---|
| Mix 1:3 | T4 | T5 |
| O1(BFref) | 10.10 | 10.15 |
|  | −0.76 | −0.69 |
| O1(BF4) | 9.06 | 9.42 |
|  | −1.80 | −1.42 |
|  | Δ 1.04 | Δ 0.73 |
| O1(BFref) | 10.10 | 10.15 |
|  | −0.76 | −0.69 |
| O1(BF5) | 9.00 | 9.38 |
|  | −1.86 | −1.46 |
|  | Δ 1.1 | Δ 0.77 |

Each tint component T1 to T6 has been tested with the oxidizing components O2 comprising any one of the buffer systems BF (comparative), BF 1 to BF 5 at a weight ratio 1:1.

The pH of the resulting hair treating composition has been measured (first value), the pH drop versus the tint component has been calculated (second value), and then the difference in pH drop between the oxidizing components (invention) and the oxidizing component (reference) has been determined (third value).

| Permanent proposition | |
|---|---|
| Mix 1:1 | T1 |
| O2(BFref) | 9.64 |
|  | −2.05 |
| O2(BF3) | 8.91 |
|  | −2.78 |
|  | Δ 0.73 |

| Mix 1:1 | T1 | T2 |
|---|---|---|
| O2(BFref) | 9.64 | 9.84 |
|  | −2.05 | −0.89 |
| O2(BF4) | 6.45 | 9.21 |
|  | −5.24 | −1.52 |
|  | Δ 3.19 | Δ 0.63 |
| O2(BFref) | 9.64 | 9.84 |
|  | −2.05 | −0.89 |
| O2(BF5) | 6.62 | 9.19 |
|  | −5.07 | −1.54 |
|  | Δ 3.02 | Δ 0.65 |

| Permanent proposition - Mix weight ratio 1:2 and 1:3 | | |
| --- | --- | --- |
| Mix 1:3 | T4 | T5 |
| O2(BFref) | 9.58 | 9.65 |
| | −1.28 | −1.19 |
| O2(BF4) | 8.7 | 9.03 |
| | −2.16 | −1.81 |
| | Δ 0.88 | Δ 0.62 |
| Mix 1:2 | T4 | |
| O2(BFref) | 9.78 | |
| | −1.08 | |
| O2(BF5) | 9.15 | |
| | −1.71 | |
| | Δ 0.63 | |
| Mix 1:3 | T4 | T5 |
| O2(BFref) | 9.58 | 9.65 |
| | −1.28 | −1.19 |
| O2(BF5) | 8.66 | 9.01 |
| | −2.2 | −1.83 |
| | Δ 0.92 | Δ 0.64 |

The invention claimed is:

1. Hair treating product, said product comprising:
(1) an oxidizing component having an acidic pH above 1.5 and comprising:
from 1% to 16% of at least one source of oxidizing agent by total weight of the oxidizing component;
a buffer system; said buffer system comprising:
a buffering acidic compound and;
a corresponding buffering alkali compound;
wherein the buffering acidic compound is phosphoric acid ($H_3PO_4$);
wherein the corresponding buffering alkali compound is selected from the group consisting of potassium dihydrogen phosphate ($KH_2PO_4$), sodium dihydrogen phosphate ($NaH_2PO_4$), dipotassium hydrogen phosphate ($K_2HPO_4$), disodium hydrogen phosphate ($Na_2HPO_4$), potassium phosphate ($K_3PO_4$), sodium phosphate ($Na_3PO_4$) and mixtures thereof;
wherein the oxidizing component comprises from 1.5% to 3% of the buffering acidic compound by total weight of the oxidizing component;
wherein the oxidizing component comprises from 0.8% to 2% of the corresponding buffering alkali compound by total weight of the oxidizing component;
wherein the weight ratio of the buffering acidic compound to the corresponding buffering alkali compound is in the range of 1:1 to 10:1; and
(2) a tint component having an alkali pH from 7.5 to 11.5 and comprising;
from 0.5% to 12% of at least one source of alkalizing agent by total weight of the tint component;
wherein the oxidizing component and the tint component are substantially free of a source of carbonate ions, carbamate ions, hydrogen carbonate ions, and mixtures thereof.

2. Hair treating product, according to claim 1, wherein the oxidizing component has a pH ranging from 2 to 4.

3. Hair treating product, according to claim 1, wherein the tint component has an alkali pH from 9 to 11.

4. Hair treating product, according to claim 1, wherein the buffering alkali compound is disodium hydrogen phosphate ($Na_2HPO_4$).

5. Hair treating product, according to claim 1, wherein the weight ratio of the buffering acidic compound to the corresponding buffering alkali compound is comprised in a range of 1:1 to 5:1.

6. Hair treating product, according to claim 1, wherein the oxidizing agent is selected from the group consisting of hydrogen peroxide, inorganic alkali metal peroxides, organic peroxides, inorganic perhydrate salt bleaching compounds, and mixtures thereof.

7. Hair treating product, according to claim 1, wherein the alkalizing agent is selected from the group consisting of ammonia; alkanolamines, guanidium salts, alkali metal and ammonium hydroxides, and mixtures thereof.

8. Hair treating product, according to claim 1, wherein the oxidizing component and/or the tint component comprises further ingredients, including solvents; chelants; radical scavengers; thickeners and/or rheology modifiers; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients; conditioning agents; ceramides; preserving agents; opacifiers and pearling agents; and mixtures thereof.

9. Hair treating product, according to claim 1, wherein the tint component comprises oxidative dyes precursors, direct dyes, and mixtures thereof.

10. Hair treating composition, said composition having a pH from 6.0 to 10.5 and comprising:
from 0.5% to 8% an oxidizing agent;
from 0.25% to 6% of an alkalizing agent;
wherein said composition is obtained from the mixing of the oxidizing component and the tint component according to claim 1.

11. Hair treating composition according to claim 5 wherein the weight ratio of the buffering acidic compound to the corresponding buffering alkali compound is comprised in a range of 1:1 to 2:1.

* * * * *